United States Patent [19]

Upton

[11] Patent Number: 4,782,048
[45] Date of Patent: Nov. 1, 1988

[54] METHOD FOR TREATING OR PREVENTING BOVINE MASTITIS

[75] Inventor: Peter Upton, Corona Del Mar, Calif.

[73] Assignee: Nelson Research & Development Co., Irvine, Calif.

[21] Appl. No.: 905,621

[22] Filed: Sep. 9, 1986

[51] Int. Cl.$^4$ .................. A61K 31/555; A61K 31/30
[52] U.S. Cl. .................................... 514/184; 514/499
[58] Field of Search ................................ 514/184, 499

[56] References Cited

FOREIGN PATENT DOCUMENTS 0046409 2/1982 European Pat. Off. .
0115130 8/1984 European Pat. Off. .

OTHER PUBLICATIONS

*Chemical Abstracts,* vol. 72 (1970) 70632t.

*Primary Examiner*—Frederick E. Waddell
*Attorney, Agent, or Firm*—Robert J. Baran; June M. Bostich

[57] ABSTRACT

The present invention provides a method for preventing or treating an animal, e.g. a cow, for mastitis, e.g. bovine mastitis, by administering to said animal a composition comprising copper ion and an organic compound having at least two hydroxyl groups and at least one unsaturated carbon-carbon bonds, e.g. ascorbic acid, in an amount effective to prevent or treat mastitis.

10 Claims, No Drawings

METHOD FOR TREATING OR PREVENTING BOVINE MASTITIS

BACKGROUND OF THE INVENTION

1. Field of the Invention

This invention relates to the use of compositions comprising copper ions in combination with an organic compound having at least two hydroxyl groups and a carbon-carbon unsaturated bond for the treatment or prevention of mastitis, e.g. bovine mastitis.

2. Description of the Art

Bovine mastitis is an infection of the udder of ruminants such as cows, mainly caused by gram positive bacteria and especially in cows in intensive milk producing units. It results in the inflammation of the mammary gland (i.e., teats and udder). The disease is particularly troublesome and of considerable economic importance because the pathogen is readily transferred from one animal to another during the milking process. Some of the main pathogens causing bovine mastitis are *Staphylococcus aureus, Streptococcus agalactiae, Streptococcus uberis, Streptoccus dysgalactiae, Escherichia coli, Aerobacter aerogenes, Klebsiella pneumoniae, Pseudomonas aeruginosa* and *Corynebacterium Pyogene*).

Any composition, useful for the treatment or prevention of bovine mastitis should be effective against most or all of the above pathogens, relatively fastacting, non-irritating to the teats or udder of the cow and, preferably, if the composition or its reaction product becomes incorporated in the milk, the composition or the reaction product should be innocuous, otherwise the milk would have to be discarded.

Bovine mastitis has so far been treated mainly by administering anti-microbial agents such as antibiotics, e.g. Penicillin G, Dihydrostreptomycin, and the like. However, it has been recently found to be very desirable to replace antibiotics by non-antibiotic drugs since the above pathogens may build up a resistance to the antibiotic resulting in pathogen strains that are more harmful to both the cows and the consumer of the milk, i.e. man.

It has thus been very important to find a method for the treatment of bovine mastitis utilizing a non-antibiotic compound which substantially would overcome the drawbacks of antibiotics utilized so far. Thus, in U.S. Pat. No. 4,401,666 to Wedig et al. it is disclosed that the use of metallic salts of pyridine-2-thione-N-oxide will treat or prevent bovine mastitis. However, at certain concentrations, these metallic salts appeared to increase the sensitivity of the cow's udder to the palpation and caused inflammation. Furthermore, milk production was reduced.

It is known that certain metal ions may be used to provide microbiocidally-active compositions. For example, U.S. Pat. Nos. 4,490,389; 4,581,374 and 4,581,379 to Nelson et al. disclose the use of solutions of copper ion and ene-diol compounds, e.g. ascorbic acid, for sterilizing contact lenses. U.S. Pat. No. 3,681,492 to Kotzbauer discloses microbiocidally-active aqueous solutions of ascorbic acid and cupric ion, stabilized by certain watersoluble amines or ammonium salts. U.S. Pat. No. 4,055,655 to Maurer et al. discloses antimicrobial agents containing a metal complex of a metal ion, e.g. copper and a polyfunctional organic ligand, e.g. ethylenediaminetetraacetic acid or citric acid. The function of the organic ligand appears to be to control the release of the metal ion from the complex. U.S. Pat. No. 4,229,430 to Fahim et al. discloses a topical oral composition, i.e. a mouth wash, comprising a zinc salt and ascorbic acid. None of the above references suggest the use of copper ion in combination with an organic polyol, having at least one carbon-carbon unsaturated bond, for the treatment or prevention of *bovine mastitis*.

BRIEF SUMMARY OF THE INVENTION

The present invention provides a method for preventing or treating an animal, e.g. a cow, for mastitis, e.g. bovine mastitis, by administering to said animal a composition comprising copper ion and an organic compound having at least two hydroxyl groups and at least one unsaturated carbon-carbon bonds, e.g. ascorbic acid, in an amount effective to prevent or treat mastitis.

DETAILED DESCRIPTION OF THE INVENTION

The compositions for use in the method of the present invention are generally provided as aqueous solutions. Therefore, the copper ion is provided by a salt that is at least partially soluble in water.

Preferably, copper is used in the form of water soluble cupric compounds; and the particularly preferred copper-containing compound is cupric chloride or cupric sulfate because both are highly soluble in water, relatively neutral, and readily available. The anhydrous or hydrate, e.g., monohydrate or dihydrate, forms of cupric chloride or cupric sulfate also may be used. Water-insoluble copper compounds, e.g., cupric acetylacetonate and cupric oleate, also may be used provided that the composition is formulated so that cupric ions become available in the final composition.

The organic compound has at least two hydroxyl radicals and preferably has only two hydroxyl radicals. The organic compound also has at least one unsaturated carbon-carbon bond, preferably only one unsaturated carbon-carbon bond, e.g. a double bond. These compounds are also at least partially soluble in water and the preferred species of such compounds may be designated as ene-diol compounds.

Typical ene-diol compounds are ascorbic acid compounds, reductic acid compounds, squaric acid compounds, dihydroxymaleic acid compounds and dihydroxyfumaric acid compounds. Typical examples of the foregoing ene-diol compounds are ascorbic acid itself, salts of ascorbic acid such as sodium ascorbate, ascorbic acid esters such as ascorbyl palmitate and any other ascorbic acid derivatives that retain the ene-diol molecular structure. The comparable acid, salt and ester forms of the other ene-diols described herein may also be used in this invention. Mixtures of ene-diols may also be used. The preferred ene-diols are ascorbic acid and dihydroxymaleic acid and their salts, e.g., sodium or potassium. The most preferred ene-diol compounds are ascorbic acid and the salts thereof.

Preferably, the aqueous solution of the copper ions and the above organic compound will be within the pH range of about 5 to about 9, more preferably from a pH of 6 to 9, for maximum activity against the above pathogens. In particular, copper ion and ascorbic acid is microbiocidallyactive against these pathogens over this pH range.

In practicing the process of the present invention, animals, preferably ruminants such as cows may be treated with an effective mastitis-treating amount of an aqueous solution comprising copper ions and the above organic compound each at concentrations sufficient, in combination, to substantially kill the above pathogens. It is to be understood that the term "an effective amount to treat or prevent mastitis", as used in the specification and claims herein, is intended to include any amount or concentration of the above-noted active compounds that will treat or prevent mastitis in animals. Of course, this amount may be changed in response to numerous variables, such as the degree of effectiveness required, whether animal is in milk or dry, and the type of carrier, if any. The aqueous composition may comprise at least about 0.1 ppm copper ion, and more preferably from 0.1 to 50 ppm, and most preferably from 1 to 25 ppm copper ion. Similarly, the organic compound will be provided at a concentration sufficient to be effective against said pathogens. The organic compound may be provided at a concentration of at least about 0.01 percent, by weight, of the aqueous solution, preferably from 0.01 to about 0.3 percent, by weight, and most preferably from 0.05 to 0.1 percent, by weight, of the aqueous solution.

The aqueous solutions, utilized in the method of the present invention and comprising ascorbic acid or a salt thereof as the organic compound, may be stagilized as disclosed in U.S. Pat. No. 3,681,492 which is hereby incorporated by reference.

While the process of the present invention is applicable to the teats of all types of mammals, the major economic impact of mastitis is in connection with dairy cows. Accordingly, the following description of the invention will be concerned mainly with cows; however, it is to be understood that this invention is contemplated with the treatment of all types of mammals, including humans.

The preferred way of administering the solution of copper ion and the organic compound is by applying it in a teat dip or spraying or the like wherein the outside of the teat is covered with an effective amount of the active compound to treat or prevent bovine mastitis.

The solution may also be administered by way of an intramammary infusion, i.e. the composition is injected into the teat through the milk canal. (In this application aqueous composition comprising copper ions and the organic compound may be emulsified in an oil to provide better wetting ofr the surfaces of the milk canal.)

The cow or other ruminant may be treated, as a preventive manner, even if it is not clear whether she suffers from mastitis (i.e. it might be that her udder is healthy). This is important, for instance, in case that it is clear that some animals of a herd are suffering from bovine mastitis and then one may want to treat all animals of said herd in order to ascertain that no further animals would be infected. Thus, prevention as well as treatment of this disease is contemplated within the scope of the invention.

Moreover, it should be understood that the process of the present invention may be performed with milking cows as well as dry cows.

Finally, the above-described aqueous solution of coper ion and the organic compound may be used to wash the teats or udder of a cow or the contact surfaces of the milking apparatus prior to milking and even the hands of the milker as a preventive measure.

To illustrate the manner in which the invention may be carried out, the following examples are given. It is understood, however, that the example is for the purpose of illustration and the invention is not to be regarded as limited to any of the specific materials or conditions therein.

EXAMPLE 1

A number of different compositions are made by blending various ingredients to form clear solutions to which an ene-diol compound is added to produce the sterilizing solutions. The following table sets forth the composition of various sterilizing solutions.

TABLE 1

| Ingredient | % Weight | | | | |
|---|---|---|---|---|---|
| | 1 | 2 | 3 | 4 | 5 |
| Part A | | | | | |
| Ammonium Chloride | 0.025 | 0.025 | 0.025 | 0.025 | 0.025 |
| Cupric Chloride dihydrate | 0.005 | 0.005 | 0.005 | 0.005 | 0.005 |
| Potassium Phosphate, monobasic | 0.530 | 0.530 | 0.530 | 0.530 | 0.530 |
| Potassium Phosphate, dibasic | 1.060 | 1.060 | 1.060 | 1.060 | 1.060 |
| Potassium Chloride | 0.300 | 0.300 | 0.300 | 0.300 | 0.300 |
| Water | 97.880 | 97.880 | 97.820 | 97.842 | 97.820 |
| Part B | | | | | |
| Dihydroxymaleic acid | 0.200 | | | | |
| Dihydroxyfumaric acid | | 0.200 | | | |
| Reductic acid | | | 0.260 | | |
| Ascorbic acid | | | | 0.238 | |
| Squaric acid | | | | | 0.260 |

When tested against the microorganisms named above, these compositions are found to be effective as microbicides.

EXAMPLE 2

The effectiveness of composition 1 in Table 1 of Example I as a microbicide was determined. Plastic discs were dipped in bacterial cultures of 10% organisms per milliliter of either staphylococcus or pseudomonas. Upon removal it was shown that $10^7$ organisms per milliliter remained in connect with the disc and the test discs were then soaked in said composition and control discs in sterile saline solution. At specific time intervals, bacterial counts were made on the discs removed from the soaking solutions and rinsed with sterile saline. The results of the study are shown in Table 3.

TABLE 3

| Disc Bacterial Culture | Bacterial count at time of removal | | |
|---|---|---|---|
| | t = 10 mins | t = 20 mins | 5 = 30 min |
| 1 Staphylococcus aureus | $<10^5$ | | |
| 2 Pseudomonas aeruginosa | $<10^5$ | | |
| 3 Staphylococcus aureus | | $<10^3$ | |
| 4 Pseudomonas aeruginosa | | $<10^3$ | |
| 5 Staphylococcus aureus | | | $<10^2$ |
| 6 Pseudomonas aeruginosa | | | $<10^2$ |
| 7 Control | $>10^7$ | | |
| 8 Control | | $>10^7$ | |
| 9 Control | | | $>10^7$ |

The results show that composition 1 is effective as a microbicide against pathogens which are believed to cause bovine mastitis.

While particular embodiments of the invention have been described it will be understood of course that the invention is not limited thereto since many obvious modifications can be made and it is intended to include within this invention any such modifications as will fall within the scope of the appended claims.

What is claimed is:

1. A method of treating an animal for mastitis which comprises administering to said animal an effective amount of copper ion, in combination with an organic compound having at least two hydroxyl radicals and at least one unsaturated carbon-carbon bond, to treat or prevent bovine mastitis.

2. The method of claim 1 wherein the administration is effected to the teats and udder of a cow.

3. The method of claim 2 wherein said copper ion and said organic compound are in aqueous solution.

4. The method of claim 3 wherein said organic compound is selected from the group consisting of ascorbic acid, squaric acid, reductic acid, dihydroxy maleic acid, dihydroxy fumaric acid and salts and esters thereof.

5. The method of claim 4 wherein said organic compound is ascorbic acid or a salt thereof.

6. The method of claim 4 wherein said aqueous solution comprises from about 1 to about 50 ppm of copper ion and from about 0.01 to about 0.3 % percent, by weight, of said organic compound.

7. The method of claim 6 wherein said solution is infused into each teat of said cow.

8. The method of claim 6 wherein said solution is applied to the outside of the teats and udder of a cow.

9. The method of claim 7 wherein said organic compound is ascorbic acid or a salt thereof.

10. The method of claim 8 wherein said organic compound is ascorbic acid or a salt thereof.

* * * * *